United States Patent
Kim et al.

(10) Patent No.: US 11,845,711 B2
(45) Date of Patent: Dec. 19, 2023

(54) METHOD FOR PREPARING ACRYLONITRILE DIMER

(71) Applicant: LG CHEM, LTD., Seoul (KR)

(72) Inventors: Wonseok Kim, Daejeon (KR); Yujin An, Daejeon (KR); Hyunchul Jung, Daejeon (KR); Sae Hume Park, Daejeon (KR); Wan Kyu Oh, Daejeon (KR); Dongmin Kim, Daejeon (KR); Kyeong Hwan Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 17/790,442

(22) PCT Filed: Jul. 7, 2021

(86) PCT No.: PCT/KR2021/008657
§ 371 (c)(1),
(2) Date: Jun. 30, 2022

(87) PCT Pub. No.: WO2022/092484
PCT Pub. Date: May 5, 2022

(65) Prior Publication Data
US 2023/0057964 A1    Feb. 23, 2023

(30) Foreign Application Priority Data
Oct. 28, 2020  (KR) .................. 10-2020-0141435

(51) Int. Cl.
| | | |
|---|---|---|
| C07C 255/08 | (2006.01) | |
| B01J 31/02 | (2006.01) | |
| C07C 253/30 | (2006.01) | |
| C07C 253/34 | (2006.01) | |
| C07C 255/09 | (2006.01) | |

(52) U.S. Cl.
CPC ......... *C07C 255/08* (2013.01); *B01J 31/0267* (2013.01); *C07C 253/30* (2013.01); *C07C 253/34* (2013.01); *C07C 255/09* (2013.01)

(58) Field of Classification Search
CPC .................................................. C07C 255/08
See application file for complete search history.

(56) References Cited

U.S. PATENT DOCUMENTS

| | | |
|---|---|---|
| 3,732,281 A | 5/1973 | Feldman et al. |
| 4,102,915 A | 7/1978 | Jennings et al. |
| 4,126,632 A | 11/1978 | Hogan et al. |
| 4,238,422 A | 12/1980 | Cozens et al. |
| 4,316,857 A | 2/1982 | Gilbert |
| 4,422,981 A | 12/1983 | Omori et al. |
| 4,841,087 A | 6/1989 | Matthews, III et al. |
| 4,952,541 A | 8/1990 | Heckle et al. |
| 4,958,042 A | 9/1990 | Shaw et al. |
| 10,759,741 B2 | 9/2020 | Aki et al. |
| 2007/0155978 A1 | 7/2007 | Jungkamp et al. |
| 2009/0099386 A1 | 4/2009 | Leconte et al. |

FOREIGN PATENT DOCUMENTS

| | | |
|---|---|---|
| EP | 0010886 A1 | 5/1980 |
| EP | 0010886 B1 | 12/1982 |
| JP | S5257122 | 5/1977 |
| JP | S5519299 | 2/1980 |
| JP | S5598149 | 7/1980 |
| JP | S57-158750 A | 9/1982 |
| JP | S61158953 | 7/1986 |
| JP | H05286918 | 11/1993 |
| JP | 2888392 B2 | 5/1999 |
| JP | 2007519673 | 7/2007 |
| JP | 2008522964 | 7/2008 |
| JP | 4386922 B2 | 12/2009 |
| JP | 4579297 B2 | 11/2010 |
| WO | 93/10082 A1 | 5/1993 |

OTHER PUBLICATIONS

Jennings, et al. (1995). The Catalytic Dimerisation of Acrylonitrile: Deactivation of Phosphinite Catalysts by Alcoholysis. ACA, vol. 130, Issue 2, pp. 175-185.

*Primary Examiner* — Golam M Shameem

(74) *Attorney, Agent, or Firm* — BRYAN CAVE LEIGHTON PAISNER LLP

(57) ABSTRACT

A method for preparing an acrylonitrile dimer according to the present disclosure makes it is possible to efficiently recover an acrylonitrile dimerization catalyst while reducing the process load.

10 Claims, 3 Drawing Sheets

[FIG. 1]
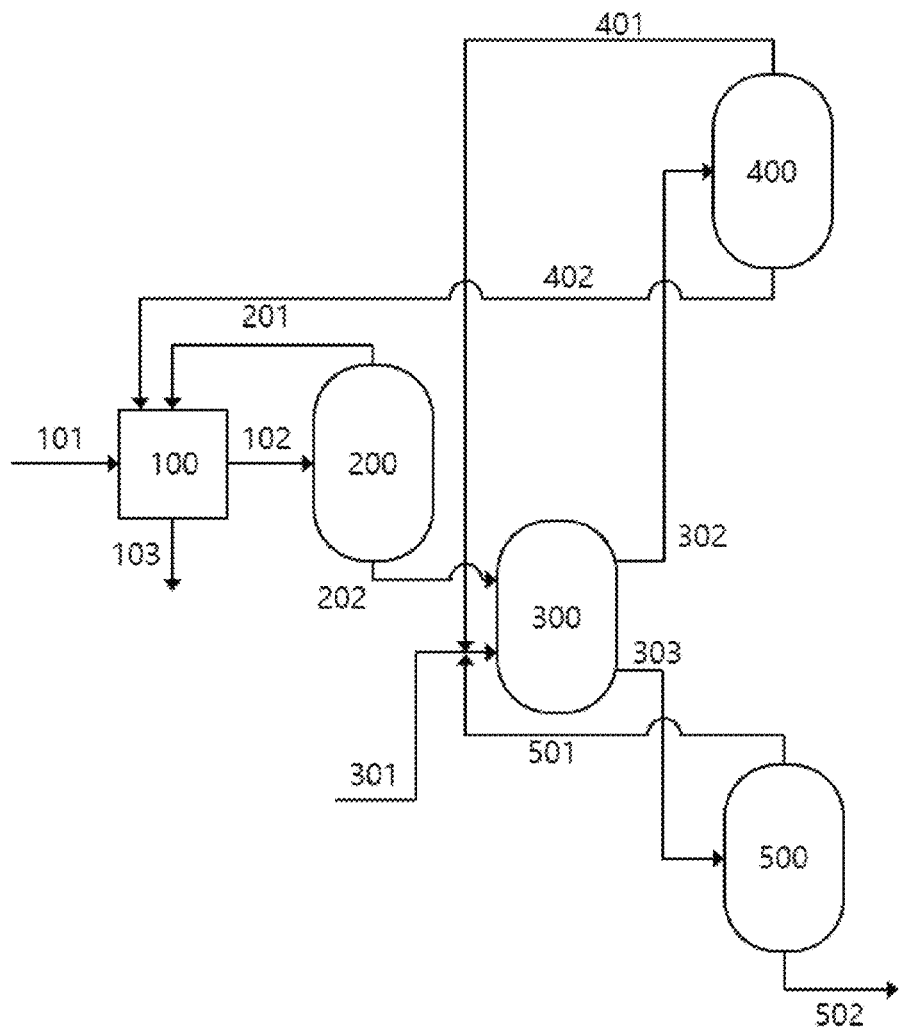

[FIG. 2]
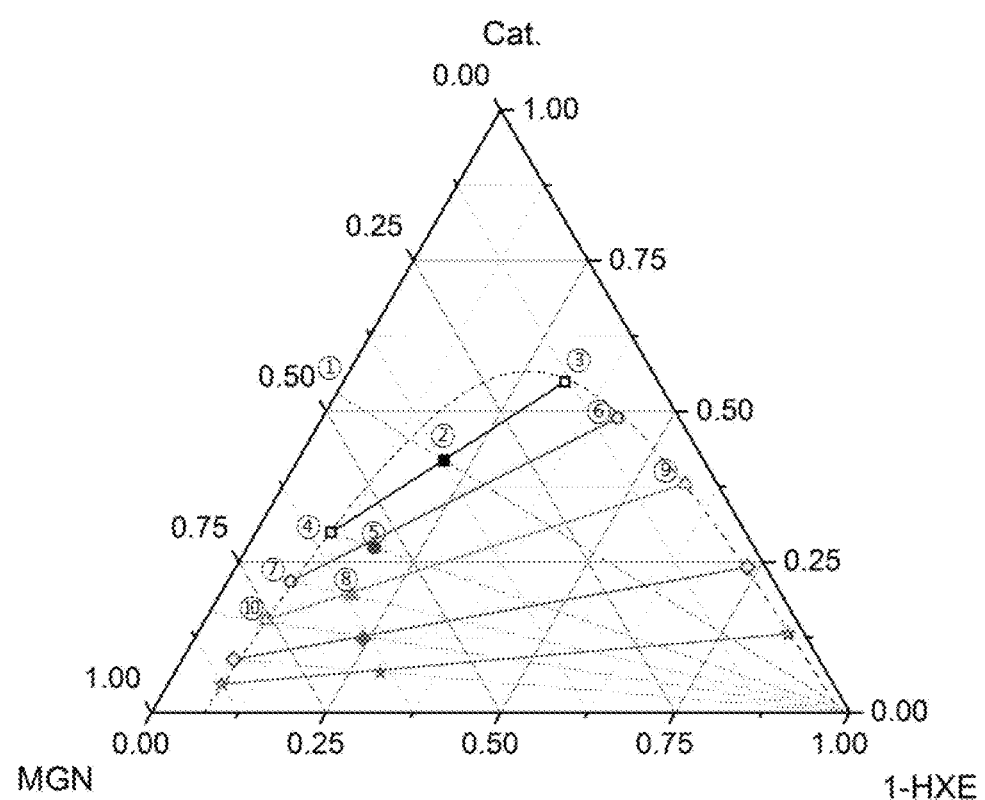

[FIG. 3]
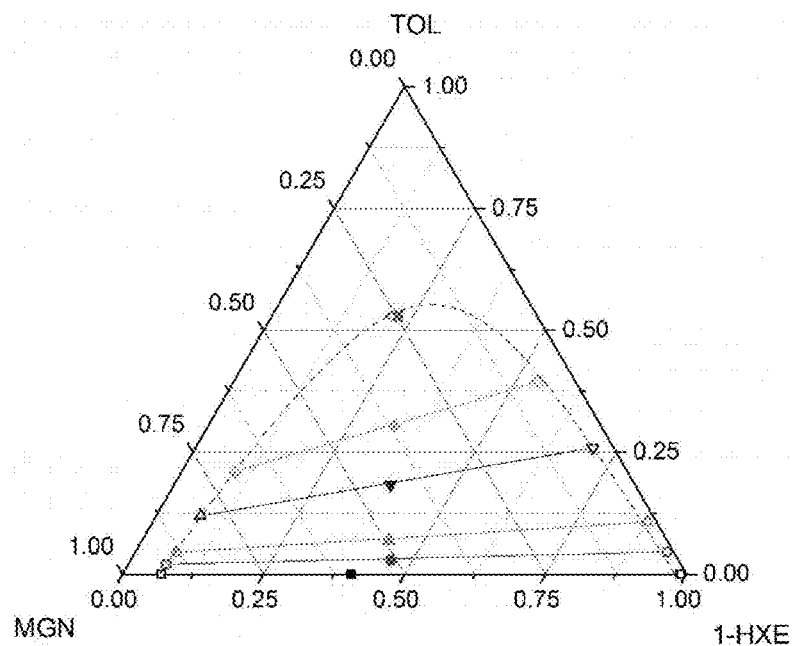
[FIG. 4]
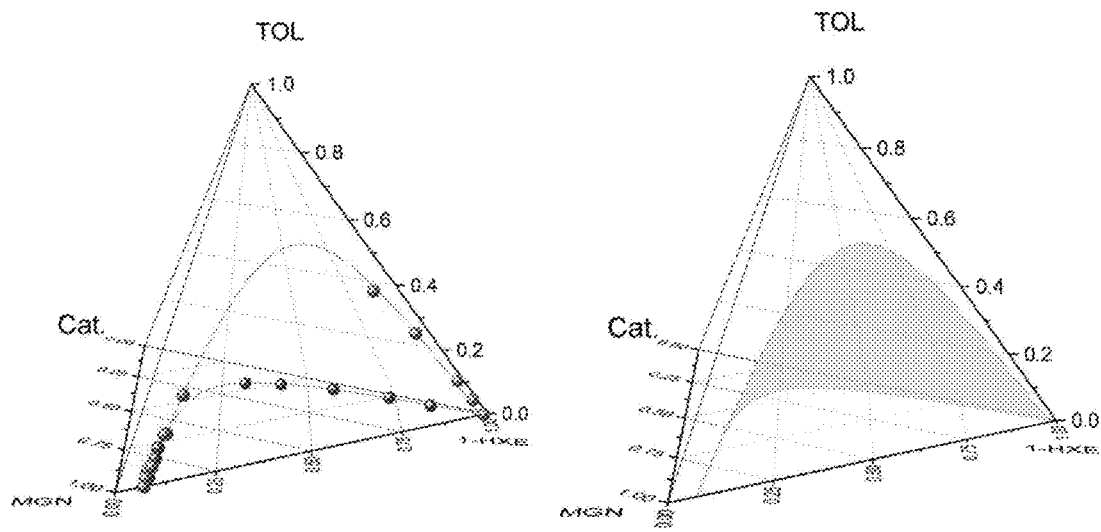

METHOD FOR PREPARING ACRYLONITRILE DIMER

The present application is a National Phase entry pursuant to 35 U.S.C. § 371 of International Application No. PCT/KR2021/008657 filed on Jul. 7, 2021, and claims priority to and the benefit of Korean Patent Application No. 10-2020-0141435 filed on Oct. 28, 2020 with the Korean Intellectual Property Office, the disclosures of which are incorporated herein by reference in its entirety.

FIELD

The present disclosure relates to a method for preparing an acrylonitrile dimer capable of efficiently recovering an acrylonitrile dimerization catalyst while reducing the process load.

BACKGROUND

Acrylonitrile dimer is commonly referred to as 1,4-dicyanobutene (DCB), 1,4-dicyanobutadiene, adiponitrile, and the like, which are linear compounds having 6 carbon atoms prepared by dimerization of acrylonitrile. Acrylonitrile dimer is usefully used as an intermediate for preparing hexamethylenediamine which is the main monomer of nylon 66.

Acrylonitrile dimers can be prepared by reacting acrylonitrile in a solvent capable of providing a proton in the presence of ruthenium or phosphorus-based catalyst. The main product of the dimerization reaction is 1,4-dicyanobutene (DCB), and a small amount of methylene glutaronitrile (MGN) can be produced as a by-product. In the reaction mixture after the reaction, components such as MGN, unreacted acrylonitrile, catalyst, and reaction solvent are mixed together with DCB which is the main product, and a pure acrylonitrile dimer can be obtained through a purification process.

Since the catalyst used for the preparation of the acrylonitrile dimer is an expensive compound and has a great influence on the unit production price, an attempt has been made to recover and reuse the catalyst after the reaction. Therefore, as a method of purifying the reaction mixture after the acrylonitrile dimerization reaction, a method of separating the catalyst by distilling acrylonitrile dimer, or a method of extracting the catalyst from the reaction mixture using an extraction solvent has been proposed.

However, in the case of a distillation method, since the boiling point of acrylonitrile dimer is as high as about 254° C., there is a problem that distillation at high temperature is unavoidable and a side reaction occurs. In addition, in the case of the extraction method, the affinity between the acrylonitrile dimer and the catalyst is high and thus, separation is difficult, and a considerable amount of the reaction solvent of acrylonitrile is present, which causes a problem that the process load is increased.

SUMMARY

It is an object of the present disclosure to provide a method for preparing an acrylonitrile dimer capable of efficiently recovering an acrylonitrile dimerization catalyst while minimizing a side reactions and reducing the process load.

In order to achieve the above object, the present disclosure provides a method for preparing acrylonitrile dimer comprising the steps of:

1) supplying acrylonitrile, a reaction solvent and a catalyst to a reactor;
2) performing a reaction of the materials supplied to the reactor, and supplying the reaction product to a first distillation column;
3) distilling the materials supplied to the first distillation column, recovering acrylonitrile and the reaction solvent at an upper part of the first distillation column and supplying the acrylonitrile and the reaction solvent to the reactor, recovering remaining materials at a lower part of the first distillation column and supplying the remaining materials to an extraction column;
4) mixing the extraction solvent with the materials supplied to the extraction column to form separate layers, recovering an upper layer liquid containing the catalyst and the extraction solvent and supplying the upper layer liquid to a second distillation column, and recovering a lower layer liquid containing the remaining materials and supplying the lower layer liquid to a third distillation column;
5) distilling the material supplied to the second distillation column, recovering the extraction solvent at an upper part of the second distillation column, supplying the extraction solvent to the extraction column, recovering the catalyst in a lower part of the second distillation column, and supplying the catalyst to the reactor; and
6) distilling the material supplied to the third distillation column, recovering the extraction solvent at an upper part of the third distillation column, supplying the extraction solvent to the extraction column, and recovering a composition containing acrylonitrile dimer at a lower part of the third distillation column.

BRIEF DESCRIPTION OF THE DRAWINGS

FIG. 1 schematically shows a process flow chart of a method for preparing acrylonitrile dimer according to the present disclosure.

FIGS. 2 and 3 show the phase diagram for a three-component system according to the embodiment of the present disclosure.

FIGS. 4A and 4B are phase diagrams for a four-component system according to FIGS. 2 and 3.

DETAILED DESCRIPTION

Hereinafter, the present disclosure will be described in detail for each step.

(Step 1)

Step 1 of the present disclosure is a step of supplying acrylonitrile, a reaction solvent and a catalyst to a reactor, which is a step of preparing the dimerization reaction of acrylonitrile.

The acrylonitrile, reaction solvent, and catalyst are supplied to a reactor 100 via a transfer line 101, and a supply quantity of respective materials can be appropriately adjusted. The reaction solvent is not particularly limited as long as it is a solvent for the dimerization reaction of acrylonitrile. Preferably, the reaction solvent includes toluene. More preferably, the reaction solvent includes toluene and isopropyl alcohol. In addition, the catalyst is a catalyst for the dimerization reaction of acrylonitrile, and is not particularly limited as long as it is a catalyst used in the art.

(Step 2)

Step 2 of the present disclosure is a step of performing a reaction of the materials supplied to the reactor 100, and supplying the reaction product to a first distillation column 200 by transfer line 102.

The reaction temperature of step 2 is preferably 30 to 90° C. When the reaction temperature is less than 30° C., the temperature is too low and thus, the reaction is not sufficiently proceeded, and when the reaction temperature is greater than 90° C., the efficiency of the reaction does not substantially increase. Preferably, the reaction temperature is 40° C. or more, or 50° C. or more, and 80° C. or less, or 70° C. or less.

The reaction pressure of step 2 is preferably 0.5 bar to 2 bar, and more preferably, normal pressure (1 bar).

The reaction time of step 2 is preferably 10 minutes to 10 hours. When the reaction time is less than 10 minutes, the reaction is not sufficiently conducted, and when the reaction time is greater than 10 hours, the reaction is not substantially advanced further. Preferably, the reaction time is 30 minutes or more, 1 hour or more, or 2 hours or more, and 9 hours or less, 8 hours or less, 7 hours or less, 6 hours or less, or 5 hours or less.

Meanwhile, depending on the reaction conditions of step 2, an insoluble oligomer may be generated as a product, which may be removed by a transfer line 103.

(Step 3)

Step 3 of the present disclosure is a step of distilling the materials supplied to the first distillation column 200, recovering acrylonitrile and the reaction solvent at the upper part of the first distillation column and supplying them to the reactor via transfer line 201, recovering remaining materials at the lower part of the first distillation column 200 and supplying them to an extraction column 300 by transfer line 202.

In the reactor 100, as the product of the dimerization reaction of acrylonitrile, in addition to acrylonitrile dimer, a trimer, a tetramer and an oligomer of acrylonitrile are produced as by-products, and unreacted acrylonitrile, a reaction solvent (toluene and isopropyl alcohol) and a catalyst are included.

Step 3 of the present disclosure is a step of distilling unreacted acrylonitrile having a small molecular weight and a reaction solvent (toluene and isopropyl alcohol) among the materials contained in the product of the above reaction and separating them. It is important to separate and reuse the catalyst in the dimerization reaction step of acrylonitrile, and conventionally, the catalyst was most preferentially separated from the dimerization reaction product of acrylonitrile. However, since the method separates the catalyst in the presence of a large amount of reaction solvent contained in the dimerization reaction product of acrylonitrile, there is a problem that the process load is high.

Therefore, unlike conventional approaches, the present disclosure has an effect of reducing the load of the catalyst separation process by preferentially distilling and removing the reaction solvent. In addition, since the reaction solvent and the unreacted acrylonitrile have similar boiling points, when the reaction solvent is distilled, unreacted acrylonitrile can also be distilled together, whereby the recovered reaction solvent and unreacted acrylonitrile can be recycled to the reactor 100.

The material is separated through distillation in the first distillation column 200, and acrylonitrile and the reaction solvent are recovered at the upper part of the first distillation column 200 and supplied to the reactor 100 via a transfer line 201. The remaining materials are recovered at the lower part of the first distillation column 200 and supplied to an extraction column 300 via a transfer line 202. At this time, in the transfer line 202, it is preferable that the materials are cooled at the temperature of the lower part of the first distillation column 200 and then supplied to the extraction column 300, and the cooled temperature may be 30 to 60° C.

Preferably, 70 wt. % or more of the reaction solvent used in step 1 is recovered at the upper part of the first distillation column. Therefore, since the reaction solvent is removed before the catalyst separation process described later, the load of the process can be reduced, and the reaction solvent may also be recycled to step 1. More preferably, 75 wt. % or more, 80 wt. % or more, 85 wt. % or more, 90 wt. % or more, or 95 wt. % or more of the reaction solvent used in step 1 is recovered at the upper part of the first distillation column.

In addition, in order to effectively recover the reaction solvent at the upper part of the first distillation column 200, it is preferable that the temperature of the upper part of the first distillation column 200 is 10° C. to 50° C., and the temperature of the lower part is 60° C. to 200° C. In particular, the temperature of the lower part of the first distillation column 200 is important. When the temperature of the lower part of the first distillation column 200 is less than 60° C., the recovery rate of the reaction solvent falls, and when the temperature of the lower part of the first distillation column 200 is greater than 200° C., there is a risk that the acrylonitrile dimer will further react with the catalyst. More preferably, the temperature of the lower part of the first distillation column 200 is 90 to 130° C., or 100 to 120° C.

(Step 4)

Step 4 of the present disclosure is a step of mixing the extraction solvent with the materials supplied to the extraction column 300 to separate layers, recovering an upper layer liquid containing the catalyst and the extraction solvent and supplying it to a second distillation column 400 by transfer line 302, and recovering a lower layer liquid containing remaining materials and supplying it to a third distillation column 500 by transfer line 303.

The materials supplied to the extraction column 300 include an acrylonitrile dimerization catalyst, and the acrylonitrile dimerization catalyst is separated through step 4. In particular, as described above, since a considerable amount of the reaction solvent was removed through step 3, the process load of step 4 is significantly reduced.

The extraction solvent is used for extracting the acrylonitrile dimerization catalyst, and it is not particularly limited as long as it does not dissolve the remaining materials while dissolving the acrylonitrile dimerization catalyst. Preferably, 1-hexene is used as the extraction solvent.

The extraction solvent is supplied to the extraction column 300 via a transfer line 301, and as will be described later, the used extraction solvent is recovered again and recycled to the extraction column 300. Layer separation occurs in the extraction column 301 by the extraction solvent, and the upper layer liquid containing the extraction solvent and the acrylonitrile dimerization catalyst is supplied to a second distillation column 400 via a transfer line 302, and the lower layer liquid containing the remaining materials is supplied to a third distillation column 500 via a transfer line 303.

(Step 5)

Step 5 of the present disclosure is a step of distilling the material supplied to the second distillation column 400, recovering the extraction solvent at the upper part of the second distillation column 400, supplying it to the extraction column 300 by transfer line 401, recovering the catalyst at the lower part of the second distillation column 400, and supplying it to the reactor 100 by transfer line 402.

Since the material supplied to the second distillation column 400 is an extraction solvent and an acrylonitrile dimerization catalyst, it is distilled and reused. Specifically, the extraction solvent is recovered at the upper part of the second distillation column 400 and recycled to the extraction column 300 via a transfer line 401. The acrylonitrile dimerization catalyst is recovered at the lower part of the second distillation column 400 and recycled to the reactor 100 via a transfer line 402.

(Step 6)

Step 6 of the present disclosure is a step of distilling the material supplied to the third distillation column 500, recovering the extraction solvent at the upper part of the third distillation column 500, supplying it to the extraction column 300 by transfer line 501, and recovering a composition containing acrylonitrile dimer at the lower part of the third distillation column 500.

Since the extraction solvent is contained even in the material supplied to the third distillation column 500, it is distilled and reused, and the remainder recovers a composition comprising an acrylonitrile dimer as a final product. Specifically, the extraction solvent is recovered at the upper part of the third distillation column 500 and recycled to the extraction column 300 via a transfer line 501. The composition containing the acrylonitrile dimer is recovered at the lower part of the third distillation column 500 and finally recovered via a transfer line 502.

Meanwhile, the method may further include a step of separating and/or purifying acrylonitrile dimer from the composition containing the recovered acrylonitrile dimer, if necessary.

The method for preparing acrylonitrile dimer according to the present disclosure has the feature that it is possible to efficiently recover the acrylonitrile dimerization catalyst while reducing the process load.

EXAMPLES

Hereinafter, embodiments of the present disclosure will be described in more detail by way of examples. However, the examples described below are for illustrative purposes only, and the content of the present disclosure is not limited thereby.

In the following Examples, acrylonitrile dimer was prepared as follows by using the apparatus having the configuration as shown in FIG. 1.

Experimental Example 1: Evaluation of Toluene Recovery Rate According to the Set Temperature of the First Distillation Column Acrylonitrile (2.43 g), toluene (8.68 g), isopropyl alcohol (0.78 g) and a catalyst (ethyl diphenylphosphinite; 0.53 g) were supplied to a reactor 100 and allowed to react under conditions of 60° C. and 1 bar for 3 hours. Then, the reaction product was transferred to a first distillation column 200.

The upper and lower parts of the first distillation column 200 were adjusted to 60 torr and 100 torr, respectively, and the temperatures of the upper and lower parts were set as shown in Table 1 below, and distilled. At this time, the temperature of the lower part of the first distillation column 200 was adjusted with a reboiler provided at the lower end of the first distillation column 200. The material was recovered at the upper part and the lower part of the first distillation column, respectively, and then, the content of toluene in the recovered material was analyzed and shown in Table 1 below.

TABLE 1

|  | Temperature of the lower part of the first distillation column | Temperature of the upper part of the first distillation column | Upper part of the first distillation column (toluene recovery rate[1]) | Lower part of the first distillation column (toluene composition[2]) |
| --- | --- | --- | --- | --- |
| #1-1 | 200° C. | 26° C. | 100% | 0 wt. % |
| #1-2 | 120° C. | 24° C. | 96% | 14.16 wt. % |
| #1-3 | 60° C. | 19° C. | 37% | 72.21 wt. % |

[1]Total weight of toluene recovered relative to the total weight of toluene charged into the reactor 100
[2]Weight of toluene relative to the total weight of the composition recovered at the lower part of the first distillation column As shown in Table 1, it was confirmed that when the temperature of the lower part of the first distillation column was set to 200° C. (#1-1), the whole amount of toluene could be recovered, and it was confirmed that even when the temperature was set to 120° C. (#1-2), toluene could be recovered at 96 wt. %. However, it was confirmed that when the temperature was set to 60° C., the toluene recovery rate was low, and most of toluene was recovered at the lower part of the first distillation column.

Example 2: Evaluation of Dimer Loss Rate and Catalyst Loss Rate According to the Set Temperature of the Reboiler of the First Distillation Column As the operating temperature of the reboiler of the first distillation column increases and the residence time increases, the recovery rate of unreacted acrylonitrile and the reaction solvent increases, but at the same time, side reactions are also promoted. Since the loss of dimer and catalyst increases when a side reaction proceeds, it is performed in the same manner as in Example 1, and the degree of side reaction according to the operating temperature and residence time of the reboiler of the first distillation column was evaluated as shown in Table 2 below.

TABLE 2

|  | #2-1 | | | | #2-2 | | | | #2-3 | | | |
| --- | --- | --- | --- | --- | --- | --- | --- | --- | --- | --- | --- | --- |
| Sample No. | T1-0 | T1-1 | T1-2 | T1-3 | T2-0 | T2-1 | T2-2 | T2-3 | T3-0 | T3-1 | T3-2 | T3-3 |
| Heating time(min) | 0 | 10 | 20 | 30 | 0 | 10 | 20 | 30 | 0 | 10 | 20 | 30 |
| Heating temperature(° C.) | 120 | 120 | 120 | 120 | 120 | 120 | 120 | 120 | 60 | 60 | 60 | 60 |
| Toluene concentration in solution (wt. %) | 0 | 0 | 0 | 0 | 13.61 | 13.35 | 13.65 | 13.92 | 0 | 0 | 0 | 0 |

TABLE 2-continued

| | #2-1 | | | #2-2 | | | | #2-3 | | | |
|---|---|---|---|---|---|---|---|---|---|---|---|
| Residual amount relative to MGN at the initial stage (%) | 98.42 | >99 | 93.01 | 88.87 | 100.44 | 105.08 | 99.80 | 95.36 | >99 | >99 | >99 | >99 |
| Residual amount relative to catalyst at the initial stage (%) | 98.18 | >99 | 95.51 | 90.01 | 97.22 | 101.33 | 96.09 | 91.62 | >99 | >99 | >99 | >99 |

In the #2-1, the operating temperature was set to 120° C. under toluene-free conditions (including only dimer (MGN, etc.) and catalyst), and when heated for 20 minutes, about 7% of a dimer loss occurred and about 4.5% of a catalyst loss occurred. In the #2-2, the operating temperature was set to 120° C. under conditions similar to the toluene concentration of about 14 wt. % of #1-2 of Example 1, and when heated for 20 minutes, about 0.2% of a dimer loss occurred and about 3.9% of the catalyst loss occurred. Comparing the results of #2-1 and #2-2 above, it was confirmed that when heated at the same 120° C. for the same time, the side reaction was suppressed due to the presence of toluene.

On the other hand, in the #2-3, the operating temperature was set to 60° C. under toluene-free conditions (including only dimer (MGN, etc.) and catalyst), and even when heated for 30 minutes or more, no loss of dimer and catalyst was observed. However, when the operating temperature was set to 60° C. as in #1-3 of Example 1, a large amount of toluene was moved to the subsequent catalytic process, which caused a problem that the load increased. Therefore, considering both the results of Example 1 and Example 2, it was confirmed that when the operating temperature was set to about 120° C., toluene could be effectively recovered and side reactions could be reduced.

Example 3: Recovery of a Composition Containing Acrylonitrile Dimer

In order to recover acrylonitrile dimer from the product recovered at the lower part of the first distillation column, the following two experiments were performed.

(1) LLE Experiment of Dimer-Catalyst-Hexene Three-Component System

Among the dimer (MGN, etc.), catalyst and toluene, which are materials contained in the product recovered at the lower part of the first distillation column, a composition containing a dimer and a catalyst (weight ratio of 52:48) was charged into an extraction column 300, and the temperature condition was maintained at 50° C. The extraction solvent 1-hexene was charged into the extraction column 300, and phase separation was confirmed. Then, the extract layer was collected (raffinate residue), and the extraction solvent was added five times in total in the order such as addition of 1-hexene again, and the composition and partition coefficient resulting therefrom were as shown in FIG. 2 and Table 3 below.

TABLE 3

| | Mixture | | | Extract | | | Raffinate | | | Partition Ratio |
|---|---|---|---|---|---|---|---|---|---|---|
| | $x_{1\text{-}HXE}$ | $x_{MGN}$ | $x_{cat}$ | $x_{1\text{-}HXE}$ | $x_{MGN}$ | $x_{cat}$ | $x_{1\text{-}HXE}$ | $x_{MGN}$ | $x_{cat}$ | $x_{cat,\,Ext}/x_{cat,\,Raf}$ |
| 1 | 0.242 | 0.635 | 0.123 | 0.733 | 0.025 | 0.241 | 0.073 | 0.839 | 0.088 | 2.73 |
| 2 | 0.294 | 0.639 | 0.067 | 0.846 | 0.023 | 0.131 | 0.077 | 0.876 | 0.047 | 2.76 |
| 3 | 0.189 | 0.616 | 0.194 | 0.574 | 0.046 | 0.380 | 0.088 | 0.758 | 0.154 | 2.47 |
| 4 | 0.235 | 0.636 | 0.129 | 0.697 | 0.033 | 0.270 | 0.154 | 0.721 | 0.124 | 2.17 |
| 5 | 0.303 | 0.595 | 0.103 | 0.789 | 0.022 | 0.190 | 0.224 | 0.680 | 0.096 | 1.97 |

As shown in FIG. 2, 1-hexene was added to a composition of ①, and the composition of the entire mixture was moved along the black dotted line, so that a composition of ② was formed. Then, by the phase separation, an extract layer having a composition of ③ and a raffinate layer having a composition of ④ were observed, and one tie line could be formed. Then, 1-hexene was added to the raffinate layer having the composition of ④, and the mixture composition was moved along the red dotted line, so that a composition of ⑤ was formed. Then, by the phase separation, an extract layer having a composition of ⑥ and a raffinate layer having a composition of ⑦ could be obtained. By adding 1-hexene by the same way, the mixture having a composition of ⑧ was phase-separated, and an extract layer having a composition of ⑨ and a raffinate layer having a composition of ⑩ could be obtained. This process was repeated 5 times in total, and 5 tie lines were confirmed. The partition coefficient appeared in the range of 2.73 to 2.76, and tended to increase as the catalyst concentration decreased.

Therefore, it can be confirmed that the acrylonitrile dimerization catalyst can be efficiently recovered by the above.

(2) LLE Experiment of Dimer-Toluene-Hexene 3-Component

Among the dimer (MGN, etc.), catalyst and toluene, which are the materials contained in the product recovered at the lower part of the first distillation column, a composition containing a dimer and toluene was charged into the extraction column 300, and the temperature condition was maintained at 50° C. The extraction solvent 1-hexene was charged into the extraction column 300, and the phase separation was confirmed. The extract layer was collected (raffinate residue), and the extraction solvent was added 5 times in total in the order such as addition of 1-hexene again. Accordingly, the composition and partition coefficient resulting therefrom were as shown in FIG. 3 and Table 4 below.

TABLE 4

| | Mixture | | | Extract | | | Raffinate | | | Partition Ratio |
|---|---|---|---|---|---|---|---|---|---|---|
| | $x_{1\text{-}HXE}$ | $x_{MGN}$ | $x_{TOL}$ | $x_{1\text{-}HXE}$ | $x_{MGN}$ | $x_{TOL}$ | $x_{1\text{-}HXE}$ | $x_{MGN}$ | $x_{TOL}$ | $x_{cat,\,Ext}/x_{TOL,\,Raf}$ |
| 1 | 0.461 | 0.510 | 0.028 | 0.942 | 0.012 | 0.045 | 0.067 | 0.912 | 0.020 | 2.25 |
| 2 | 0.437 | 0.493 | 0.069 | 0.877 | 0.016 | 0.107 | 0.073 | 0.882 | 0.045 | 2.35 |
| 3 | 0.384 | 0.434 | 0.183 | 0.705 | 0.037 | 0.259 | 0.079 | 0.802 | 0.119 | 2.17 |
| 4 | 0.329 | 0.366 | 0.305 | 0.540 | 0.067 | 0.394 | 0.094 | 0.695 | 0.210 | 1.87 |
| 5 | 0.224 | 0.245 | 0.530 | 0.213 | 0.257 | 0.530 | — | — | — | — |

(3) LLE Experiment of 4-Component System

When a quaternary plot was derived based on the LLE data of two 3-component system ("Liquid Extraction" by Robert E. Treybal), it was the same as the graph in FIG. 4A. Through this phase diagram, the phase separation composition when the catalyst and toluene were present together could also be inferred and it appeared on the blue-green plane of the graph of FIG. 4B.

The invention claimed is:

1. A method for preparing acrylonitrile dimer comprising the steps of:
   1) Supplying acrylonitrile, a reaction solvent and a catalyst to a reactor;
   2) Performing a reaction of the materials supplied to the reactor, and supplying the reaction product to a first distillation column;
   3) Distilling the materials supplied to the first distillation column, recovering acrylonitrile and the reaction solvent at an upper part of the first distillation column and supplying the acrylonitrile and the reaction solvent to the reactor, recovering remaining materials at a lower part of the first distillation column and supplying the recovered remaining materials to an extraction column;
   4) Mixing the extraction solvent with the materials supplied to the extraction column to form separate layers, recovering an upper layer liquid containing the catalyst and the extraction solvent and supplying the upper layer liquid to a second distillation column, and recovering a lower layer liquid containing the remaining materials and supplying the lower layer liquid to a third distillation column;
   5) Distilling the material supplied to the second distillation column, recovering the extraction solvent at an upper part of the second distillation column, supplying the reaction solvent to the extraction column, recovering the catalyst at a lower part of the second distillation column, and supplying the catalyst to the reactor; and
   6) Distilling the material supplied to the third distillation column, recovering the extraction solvent at an upper part of the third distillation column, supplying the extraction solvent to the extraction column, and recovering a composition containing acrylonitrile dimer at a lower part of the third distillation column.

2. The method of claim 1, wherein the reaction solvent comprises toluene.

3. The method of claim 1, wherein the reaction temperature in step 2 is 30 to 90° C.

4. The method of claim 1, wherein the reaction time of step 2 is 10 minutes to 10 hours.

5. The method of claim 1, wherein the temperature of the lower part of the first distillation column is 60° C. to 200° C.

6. The method of claim 1, wherein the temperature of the lower part of the first distillation column is 100° C. to 120° C.

7. The method of claim 1, wherein 70 wt. % or more of the reaction solvent used in step 1 is recovered at the upper part of the first distillation column.

8. The method of claim 1, wherein 75 wt. % or more of the reaction solvent used in step 1 is recovered at the upper part of the first distillation column.

9. The method of claim 1, wherein the extraction solvent is 1-hexene.

10. The method of claim 1, which further comprises a step of separating and/or purifying acrylonitrile dimer from the composition containing the recovered acrylonitrile dimer.

* * * * *